(12) United States Patent
Zhou et al.

(10) Patent No.: US 7,803,563 B2
(45) Date of Patent: Sep. 28, 2010

(54) METHOD FOR SCREENING THE RECEPTOR-LIGAND BINDING IN LIVE CELL

(75) Inventors: Zhuan Zhou, Beijing (CN); Hoping Cheng, Beijing (CN)

(73) Assignees: Shanghai Institutes for Biological Sciences, CAS, Shanghai (CN); Peking University, Beijing (CN)

( * ) Notice: Subject to any disclaimer, the term of this patent is extended or adjusted under 35 U.S.C. 154(b) by 0 days.

(21) Appl. No.: 12/298,988

(22) PCT Filed: Apr. 29, 2007

(86) PCT No.: PCT/CN2007/001451

§ 371 (c)(1),
(2), (4) Date: Mar. 9, 2009

(87) PCT Pub. No.: WO2007/128230

PCT Pub. Date: Nov. 15, 2007

(65) Prior Publication Data

US 2009/0197282 A1 Aug. 6, 2009

(30) Foreign Application Priority Data

Apr. 29, 2006 (CN) .................. 2006 1 0026241

(51) Int. Cl.
*G01N 33/53* (2006.01)
*G01N 33/567* (2006.01)
(52) U.S. Cl. ........................................ 435/7.2
(58) Field of Classification Search ............... None
See application file for complete search history.

(56) References Cited

U.S. PATENT DOCUMENTS

2003/0096322 A1   5/2003   Giuliano et al.

FOREIGN PATENT DOCUMENTS

| CN | 1687785 A | 10/2005 |
|---|---|---|
| WO | 0063418 A1 | 10/2000 |
| WO | 02/073199 A | 9/2002 |
| WO | 03040303 A2 | 5/2003 |

OTHER PUBLICATIONS

Ghosh RN et al. Biotechniques 29(1):170-175, Jul. 2000.*
Betz WJ, et al. Current Opinion in Neurobiology 6:365-371, 1996.*
Cousin MA. et al. J. Neurochemistry 73:2227-2239, 1999.*
esp@cenet English translation of the Abstract for related Chinese Application No. CN1687785, published Oct. 26, 2005 (1 page).
International Search Report and Written Opinion issued Aug. 2, 2007, in related International Application No. PCT/CN2007/001451 (12 pages).
Chen, Xiaoke, et al.; "Kiss-and-Run' Glutamate Secretion in Cultured and Freshly Isolated Rat Hippocampal Astrocytes"; The Journal of Neuroscience, Oct. 5, 2005; 25(40); pp. 9236-9243.

Chen, Xiao-Ke, et. al.; "Activation of GPCRs modulates quantal size in chromaffin cells through Gbg and PKS"; Nature Neuroscience, vol. 8, No. 9, Sep. 2005; (2005 Nature Publishing Group http://www.nature.com/natureneuroscience); pp. 1160-1168.
Conner, Sean D., et al., "Regulated Portals of Entry into the Cell", Department of Cell Biology, The Scripps Research Institute, La Jolla, CA 92037, USA; Nature Publishing Group, vol. 422 (Mar. 6, 2003), pp. 37-44. (p. 4 of the Specification).
Ferguson, Stephen S. G., "Evolving Concepts in G Protein-Coupled Receptor Endocytosis: the Role in Receptor Desensitization and Signaling"; The John P. Robarts Research Institute and Departments of Physiology, Pharmacology and Toxicology, and Medicine, University of Western Ontario, London, Ontario, Canada Pharmacol. Rev., vol. 53, No. 1, pp. 1-24 (2001). (p. 5 of the Specification).
Zhang, Chen, et al., "Calcium- and Dynamin-Independent Endocytosis In Dorsal Root Ganglion Neutrons", Neuron, vol. 42, pp. 225-236 (Apr. 22, 2004). (p. 7 of the Specification).
Go, Willliam Y., et al., "Quantitative Dynamic Multicompartmental Analysis of Cholecystokinin Receptor Movement in a Living Cell Using Dual Fluorophores and Reconstruction of Confocal Images"; Analytical Biochemistry 247, Article No. AB972104, pp. 210-215 (1997). (p. 8 of the Specification).
Denk, Winfried, et al., "Two-Photon Laser Scanning Fluorescence Microscopy", Science, New Series, vol. 248, No. 4951 (Apr. 6, 1990), pp. 73-76. (p. 8 of the Specification).
Lakowicz, Joseph R., et al., "Fluorescence Lifetime Imaging", Department of Biological Chemistry, Center for Fluorescence Spectroscopy, University of Maryland School of Medicine, Baltimore, MD 21201, and Department of Pharmacology, University of Virginia School of Medicine, Charlottesville, VA 22908; Anal. Biochem. 202, pp. 316-330 (1992). (p. 8 of the Specification).
Taylor, D. Lansing, et al., "The New Vision of Light Microscopy: Lasers, electronic cameras and digital image analysis combine with the most venerable instrument of the life sciences to create new ways of seeing living cells", American Scientist, vol. 80, pp. 322-335 (1992). (p. 17 of the Specification).
Proffitt, Robert T., et al., A Fluorescence Digital Image Microscopy System for Quantifying Relative Cell Numbers in Tissue Culture Plates; Cytometry 24, pp. 204-213 (1996 Wiley-Liss, Inc.). (p. 17 of the Specification).
Proffitt, Robert T., et al., A Fluorescence Digital Image Microscopy System for Quantifying Relative Cell Numbers in Tissue Culture Plates; Cytometry 24, pp. 204-213 (1996 Wiley-Liss, Inc.). (p. 17 of the Specification) (previously submitted in IDS filed Mar. 9, 2009).

(Continued)

*Primary Examiner*—Robert Landsman
(74) *Attorney, Agent, or Firm*—Osha • Liang LLP (57) ABSTRACT

The invention relates to methods and system for detecting ligand binding to membrane receptors and endocytosis. A method for detecting ligand binding to a membrane receptor includes the steps of: incubating the cell with a dye and a ligand; and detecting dye-containing endocytic vesicles in the cell. A system for screening ligand binding to membrane receptors includes an automatic liquid handling device; an x-y stage for positioning a plate; a microscope configured to image endocytic vesicles of a cell; a software for automatic analysis of FM spots (endocytic vesicles); and a control unit configured to control the movement of the x-y stage and the microscope.

13 Claims, 9 Drawing Sheets

OTHER PUBLICATIONS

Extended European Search Report and Written Opinion issued Jun. 8, 2009, by the European Patent Office in European Application No. 07721024.3-1223 (7 pages).

EPO Communication (Office Action) issued May 25, 2010, by the European Patent Office in related European Patent Application No. 07721024.3 (3 pages).

* cited by examiner

METHOD FOR SCREENING THE RECEPTOR-LIGAND BINDING IN LIVE CELL

BACKGROUND OF INVENTION

1. Field of the Invention

The present invention relates generally to methods and systems for high throughput screening of ligand-receptor bindings in living cells.

2. Background Art

High-throughput screening (HTS) research has benefited from many technological advances over the past few years. The ability to synthesize huge chemical libraries and the availability of automated robots to assist in the screening process have enabled drug development companies to routinely screen a large number of compounds per day.

HTS in vitro and in vivo assays are essential for compound evaluation. Cell-based assays, especially those using optical endpoints, permit investigation of a wide variety of functional properties of these compounds including specific intracellular biochemical pathways, protein-protein interactions, and subcellular localization of the targets. Integration of combinatorial chemistry and HTS with contemporary pharmacology is an important part of drug discovery and development.

G protein-coupled receptors (GPCRs) are a particularly important class of cell surface receptors. The medical importance of these receptors is evidenced by the fact that more than 60% of all commercially available prescription drugs work by interacting with known GPCRs. Hundreds, if not thousands, of receptors convey messages through heterotrimeric G proteins, of which at least 17 distinct forms have been isolated. Most G protein-coupled receptors are comprised of a single protein chain that is threaded through the plasma membrane seven times. Such receptors are often referred to as seven-transmembrane receptors (STRs). More than a hundred different GPCRs have been found, including many distinct receptors that bind the same ligand, and there are likely many more GPCRs awaiting discovery. The development of new drug discovery assays to identify novel modulators of GPCRs would be of tremendous benefit.

Cell membrane receptor proteins are high value targets for therapeutic use. Examples of membrane receptors include the G-protein coupled receptors (GPCRs) and receptors of tyrosine kinases (RTKs). Membrane receptors may be involved in immune system regulation, autonomic nervous system transmission, inflammatory responses, cell differentiation and proliferation, and physiological senses such as smell and sight.

In many biological processes, ligand-receptor binding (LRB) touches off a cascade of cell signaling events. In addition to these signaling events, a common path for GPCR proteins is the internalization of the ligand-bound receptor in an endocytic vesicle. Endocytosis is also observed for a number of RTKs as well. Because of the importance of GPCRs and RTKs as targets for drug discovery, several methods have been developed to study LRB-induced endocytosis. These methods include patch-clamp measurement of cell membrane capacitance (Cm), immunochemical methods, and the use of green fluorescent protein (GFP) tags.

Membrane capacitance measurements require ion currents, which in the case of GPRCs is seldom viable. Immunochemical methods usually require large numbers of cells for the assay. Furthermore, immunoassays can take tens of minutes. GFP tagging GPCR proteins has been used, but has the following drawbacks: (i) they cannot be applied to wild-type GPCRs; (ii) the GPCR-GFP signal is too weak to monitor single endocytic vesicles; (iii) the GFP tagging may alter some properties of native GCPRs. Similar problems arise with the sensitivity and engineering GFP-tagged RTKs. Because of the importance of GPCRs and RTKs in therapeutic application, there remains a need for methods of sensitive assays that can be used in HTS screening.

SUMMARY OF INVENTION

In one aspect, embodiments of the invention relate to methods for detecting ligand binding to membrane receptors and endocytosis. A method for detecting ligand binding to one or more membrane receptors on a cell includes the steps of: incubating the cell with a dye and a ligand; and detecting dye-containing endocytic vesicles in the cell.

Another aspect of the invention relates to systems for screening ligand binding to membrane proteins. A system in accordance with one embodiment of the invention includes an automatic liquid handling device; an x-y stage for positioning a plate; a microscope configured to image endocytic vesicles in a single cell; and a control unit configured to control the movement of the x-y stage and the microscope.

Other aspects and advantages of the invention will become apparent from the following description and attached claims.

DETAILED DESCRIPTION

Embodiments of the invention provides methods and systems for screening ligand binding to membrane-bound receptors. Methods of the invention are based on detecting or monitoring endocytic vesicles resulted from ligand receptor binding (LRB). These methods are not specific to a particular receptor; instead, they are generally applicable to a wide range of membrane bound receptors that involve receptor internalization (endocytosis) after ligand binding. Examples of such receptors include G-protein coupled receptors (GPCRs) and receptors of the tyrosine kinases (RTK) family. Thus, methods of the invention have many applications, including drug screening for therapeutics that bind to various membrane receptors.

While embodiments of the invention can be applied to any receptor that is associated with receptor internalization (endocytosis), for clarity, the following description will use G-protein coupled receptors (GPCRs) and receptor of tyrosine kinase (RTK) family for illustration. However, such specific examples are not intended to limit the scope of the invention.

The seven-transmembrane G-protein-coupled receptors (GPCRs) are the largest single family of membrane receptors. These receptors transfer the extracellular signals of ligand-GPCR binding into a series of intracellular signals. See e.g., Conner et al., "*Regulated Portals of Entry into the Cell*," Nature, 422: 37-44 (2003). Agonist binding to GPCR initiates processes that include desensitization of GPCR responsiveness, the internalization of GPCRs, and the coupling of GPCRs to G protein-independent signal transduction pathways. GPCR desensitization results from G protein uncoupling in response to phosphorylation by second messenger-dependent protein kinases or G protein-coupled receptor kinases (GRKs). GRK-mediated receptor phosphorylation promotes the binding of β-arrestins, which target many GPCRs for internalization in clathrin-coated vesicles (i.e., endocytosis). See e.g., Ferguson, S. S., "*Evolving Concepts in G Protein-Coupled Receptor Endocytosis: the Role in Receptor Desensitization and Signaling*," Pharmacol. Rev., 53: 1-24 (2001). This ligand-receptor binding (LRB)-induced receptor internalization (endocytosis) involves a highly conserved domain in all GPCRs. Therefore, ligand-induced endocytosis is a common feature for most GPCRs The GPCRs are involved in many stimulus-response pathways from intercellular communication to physiological senses such as sight and smell. The diversity of function of GPCRs is matched by a wide array of ligand classes that they recognize, including proteins, small molecules, and even photons. The ubiquitous involvement of GPCRs in normal biological processes and their involvement in many pathological conditions has led to GPCRs being the target of 40-50% of modern medicinal drugs.

Receptors of tyrosine kinases (RTKs) form another big family of receptors that also involve LBR-induced endocytosis. These receptors are involved in cellular signaling pathways and regulate key cell functions such as proliferation, differentiation, anti-apoptotic signaling and neurite outgrowth. Unregulated activation of these enzymes, through mechanisms such as point mutations or over-expression, can lead to various forms of cancer as well as benign proliferative conditions. Indeed, more than 70% of the known oncogenes and proto-oncogenes code for RTKs.

Figure 1:
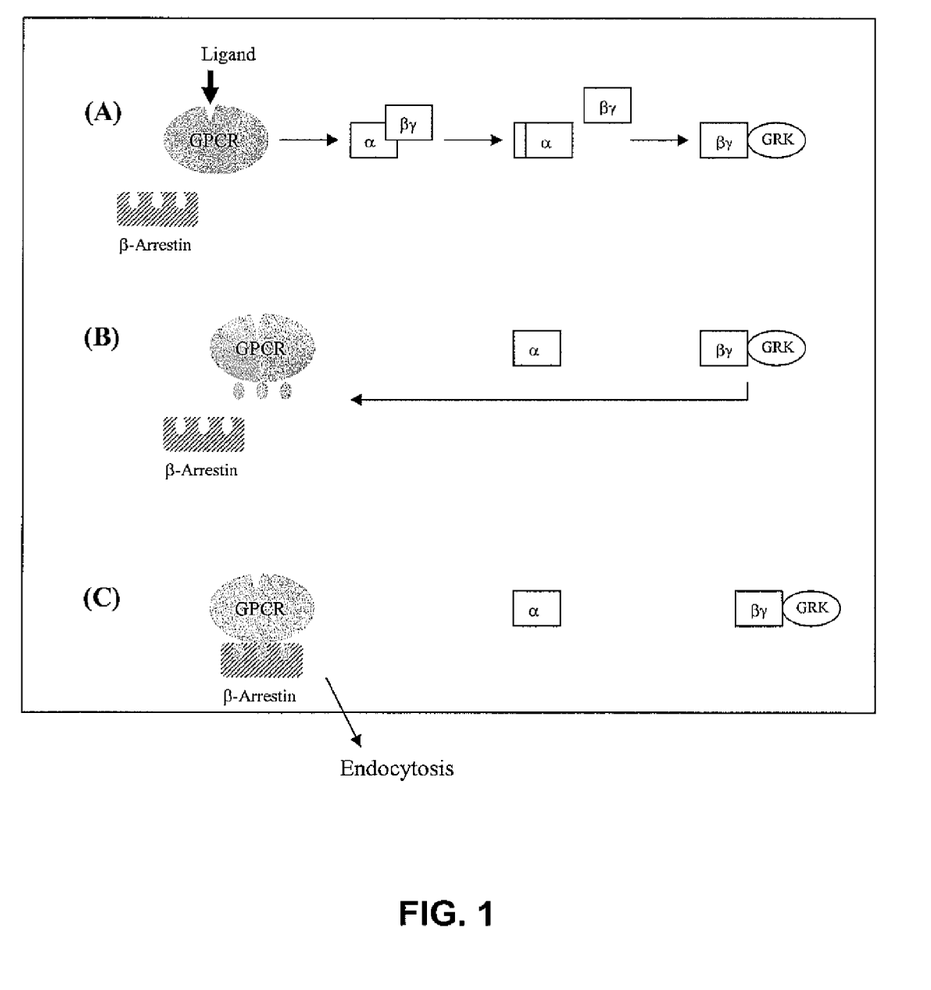
FIG. 1 illustrates binding of a ligand to a GPCR and subsequent phosphorylation by a GRK, binding of β-arrestin, and endocytosis.

LRB-induced endocytosis is well studied. The process involves the formation of vesicles that pinch off cell membrane, with the resulting vesicles entering the cell. The details of this process are illustrated in FIG. 1 for a typical GPCR. In addition to generating secondary messengers, ligand-receptor binding (LRB) to GPCR induces phosphorylation (mediated by a G protein receptor kinase (GRK)) at the C-terminal of a GPCR within the cell. β-Arrestin then binds to the phosphorylated GPCR to trigger receptor internalization via vesicle endocytosis. A similar process (receptor internalization) occurs in RTKs.

Several techniques have been developed to study the LRB-induced endocytosis process. For a small subset of GPCRs that regulate ion channels and/or intracellular calcium stores, LRB between a GPCR and its ligand produces ion currents or $[Ca^{2+}]_i$ transients in the cell. However, the majority of GPCRs do not produce any immediate ion currents, and, therefore, other techniques have been developed.

Two recently developed techniques involve labeling either the GPCR or β-arrestin with green fluorescent protein (GFP). Fluoresence resonance energy transfer (FRET) can then be used to detect LRB to GPCRs tagged with GFP. β-Arrestin tagged with GFP can also be used to detect ligand binding to GPCRs in a similar manner. Both these methods have limitations however: (i) the FRET assay cannot be applied to wild-type GPCRs; (ii) the GPCR-GFP signal is too weak to monitor single endocytic vesicles; (iii) the GFP tagging may alter some properties of native GCPRs; (iv) β-arrestin-GFP conjugates can be applied only to engineered cells expressing proper endocytic set of β-arrestin-GFP, GRK, and receptor. Because there are many types of β-arrestins, GRKs and receptors it cannot apply to native receptors. Similar issues arise in considering the available techniques to study the endocytosis of RTKs.

Two general types of physiological stimuli trigger exocytosis and endocytosis: depolarization and chemical ligands. Although there is no real-time assay for LRB, there are some real-time assays for exocytosis and endocytosis. Confocal FM imaging has been used as a real-time assay of exocytosis as well as a delayed assay (time resolution 3-5 minutes) for endocytosis in single cells. See e.g., Zhang et al., "*Calcium- And Dynamin-Independent Endocytosis In Dorsal Root Ganglion Neutrons*," Neuron, 42: 225-236 (2004). FM imaging has the advantage of showing the spatial distribution of endocytic vesicles. Another real-time assay is membrane capacitance (Cm) under whole cell recording. Cm has been used to study depolarization-induced exocytosis and endocytosis. It can also record ligand-induced exocytosis.

Methods of the invention are based on FM endocytosis imaging (FEI). Confocal imaging can be used to measure the endocytosis induced by ligand-receptor binding (LRB). The principles of FM endocytosis imaging (FEI) method are: (i) an extracellular styryl FM dye (e.g., FM2-10) is taken up by the endocytic vesicles; and (ii) the FM molecule becomes 100 times brighter after uptake into vesicles. Thus, after proper stimulation, individual FM-loaded vesicles become visible images by standard confocal microscopy.

Figure 2A:
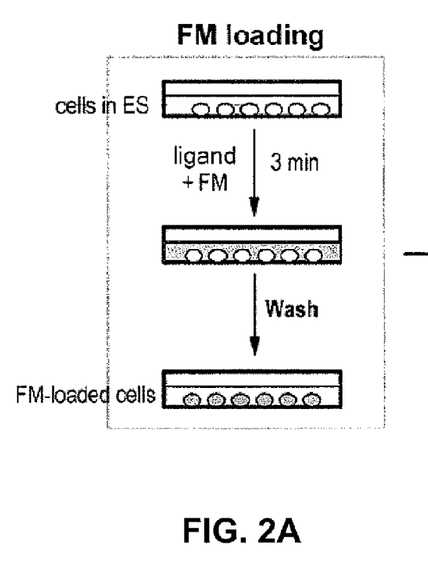
FIGS. 2A-2B illustrate the process of FM loading of cells and subsequent FM imaging.

FIG. 2A illustrate a method of the invention. As shown in FIG. 2A, a cell is treated with a solution containing a dye (e.g., an FM-dye) and a ligand that is recognized by a receptor on the cell membrane. The ligand binds to the receptor and triggers receptor internalization (endocytosis). In the endocytosis process, the FM dye is internalized in endocytic vesicles. Subsequently, the excess FM-dye may be washed away, leaving behind cells loaded with dye filled vesicles that are observable due to the fluorescent dye. Using this procedure, single vesicles in a single cell can be visualized by FM imaging. Note that while this example uses an FM dye, other suitable dyes may also be used without departing from the scope of the invention. Furthermore, since the FM dye (or other similar dye) has a substantially increased fluorescence intensity (about 100 times) once trapped in a vesicle, it may not be necessary to wash away the excess FM dye outside the cell. Therefore, some methods of the invention may not include the washing step.

The images of dye-containing (e.g., FM dye) vesicles in the cell may be visualized with any properly equipped microscope, including confocal microscopes and multi-photon microscopes. Scanning confocal microscope imaging (Go et al., Analytical Biochemistry 247:210-215 (1997)) and multiphoton microscope imaging (Denk et al., Science 248:73 (1990)) are well established methods for acquiring high resolution images of microscopic samples. The advantage of these systems lies in their shallow depth of focus, which makes it possible to resolve features of limited axial extent. For example, it is possible to resolve internal cytoplasmic features of a cell from features on the cell surface. Scanning multiphoton imaging uses short busts of pulsed laser. Therefore, it is possible to measure fluorescence lifetimes with these systems (Lakowicz et al., Anal. Biochem. 202:316-330 (1992)), providing additional capability for different detection modes. The following description uses results obtained with confocal microscopes. However, one of ordinary skill in the art would appreciate that these are for illustration only and embodiments of the invention can use any suitable microscopes.

Figure 2B:
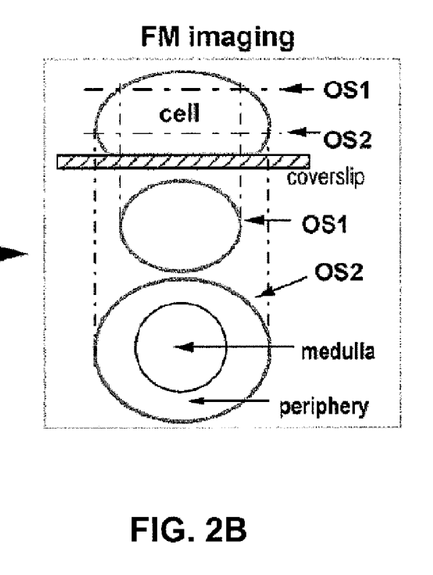

When a confocal microscope is used, the images may be takes in different optical slices (OSs) based on different focal depth. FIG. 2B shows an example, in which the cell is imaged in 1-2 μm optical slices (OSs) with a confocal microscopy. The data can be observed as the distribution of FM spots (individual vesicles) in each OS or as a global view, which is a projection overlaying the FM images from different OSs. An advantage of viewing the individual OS is the ability to track the location of the endocytic vesicles within the cell. This would permit studies of vesicle trafficking inside the cells. The advantage of the global view is the total number of vesicles are observed and, therefore, it provides a maximum sensitivity for assay use. For example, the global view may be used to monitor LRB events as a function of time—e.g., in real-time monitoring.

In accordance with some embodiments of the invention, the entire sequence from plating of cells, introducing dyes, introducing ligands, washing away the excess dye, the imaging of FM spots of the OS and the data analysis may be controlled with a processor for automation, as described in a later section. Furthermore, because FEI is an optical technique, it should be well suited to the development of a rapid high throughput bioassay. Thus, the FEI technique should prove valuable in assessing drug candidates for binding to a selected receptor (e.g., GPCR or RTK).

Examples of the FEI Bioassay

Figures 3A, 3B:
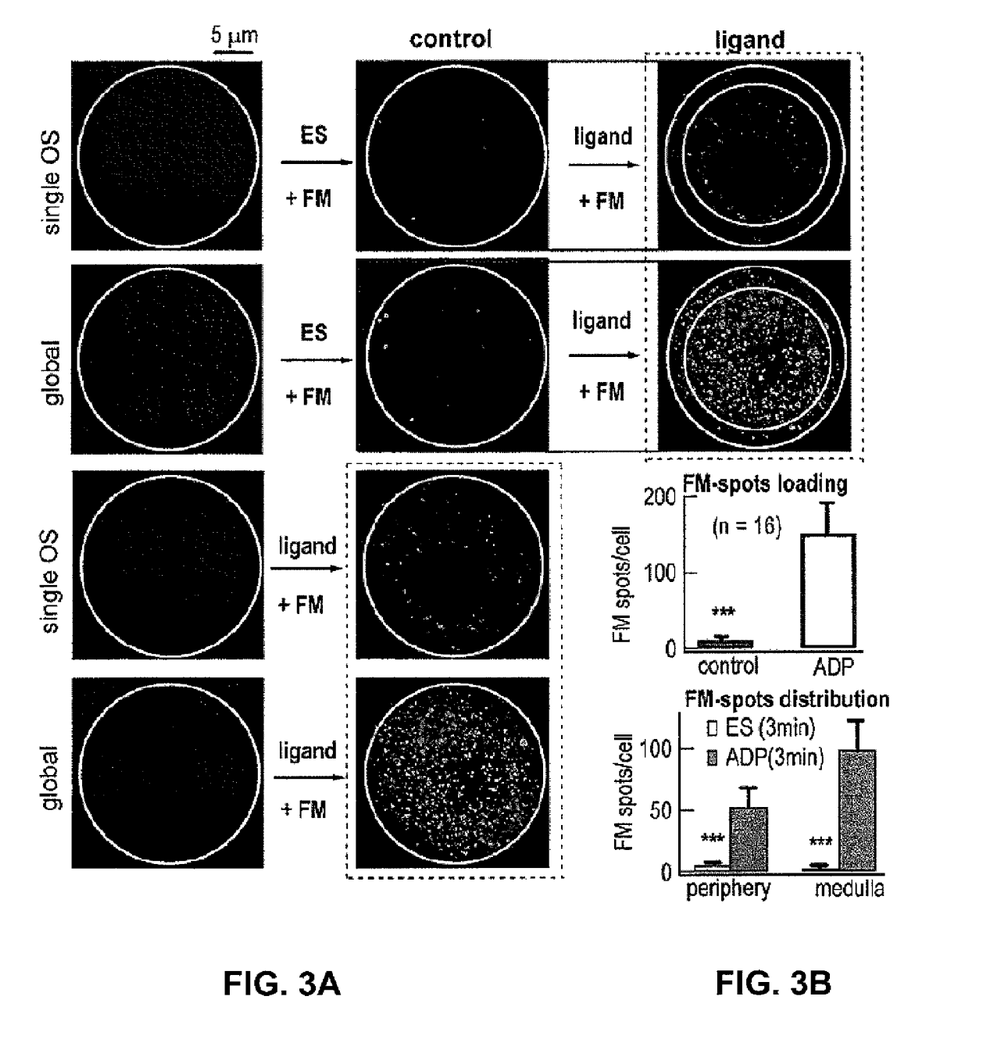
FIGS. 3A-3B show ADP-induced endocytosis in a DRG neuron visualized by the FEI technique and the data displayed in histogram.

FIG. 3A shows FM images of ADP-induced endocytosis in a single dorsal root ganglion (DRG) neuron. DRG are isolated from the lumbar and thoracic regions of Wistar rats (80-120 g, ALACCAS Inc., Shanghai) and rinsed in 4° C. DMEM solution (GIBCO Laboratories, NY) oxygenated with 95% $O_2$ and 5% $CO_2$. The ganglia are treated with 1.0 mg/ml collagenase (type IA, Sigma) and 0.3 mg/ml trypsin (type III, Sigma) at 37° C. for 40 minutes. After 5 washes in standard external solution, DRG are triturated progressively by fine fire-polished Pasteur pipettes. Cell suspensions are plated onto culture dishes. Cells are used 1-8 hours after preparation. Only small neurons (15-25 μm) without apparent process are used.

In FIG. 3A, the cell surface is marked by a white circle. The control cell was incubated with FM+ES (external solution control) for 3 min, while the test cell was incubated with FM+ADP for 3 min. The standard external solution (ES) contains: 150 mM NaCl, 5 mM KCl, 2.5 mM $CaCl_2$, 1 mM $MgCl_2$, 10 mM HEPES, and 10 mM glucose, adjusted to pH=7.4. The FM dye, for example, may be FM2-10 or FM4-64 at a suitable concentration (e.g., 10-100 μM). All experiments were carried out at room temperatures (22-25° C.). Afterwards, the FM containing solutions outside the cell were removed and the cell washed (e.g., with ES solutions, three times) to remove any dye non-specific bound to the outside of the cell. The addition and washing may be performed with fluid control or perfusion system known in the art. For example, the perfusion system sold under the trade name MPS-2 from INBIO, Inc. (Wuhan, China) was used in these experiments. MPS-2 uses electronic switching between 7 channels to provide a fast exchange time (<50 ms).

The dye-containing vesicles in the cell may be imaged with a confocal fluorescence microscope, such as Zeiss LSM 510 (Germany). Both FM2-10 and FM4-64 may be excited with a wavelength around 488 nm. FM2-10 emits at around 505-600 nm, while FM4-64 emits at a wavelength >630 nm. Therefore, when both dyes are present, it is possible to observe both dyes simultaneously using proper filtering.

It is evident from FIG. 3A that the number of FM spots, which represent endocytic vesicles, increased dramatically after adding ADP, indicating induced endocytosis by ADP binding to its GPCR, P2Y. The single OS images shown in FIG. 3A are 1 μm optical slices (OS) of the cell. The global images shown are projections of 20 OS FM images of the cell. The clarity of spatial distribution in the single OS allows one to see that more ADP-induced vesicles are located in the medulla than in the periphery of the DRG neuron. Such spatial resolution may permit studies of vesicle trafficking, if desired.

The FM spots in each OS can be counted manually or automatically, e.g., with the aid of a software. For example, the Image-Pro® Plus software from Media Cybernetics, Inc. (Silver Spring, Md.) may be used. Vesicle sizes may range from 0.04 $μm^2$ to about 1 $μm^2$ in such images. Thus, the pixel sizes of the images may be properly adjusted so that FM spots corresponding to the vesicles are counted. One of ordinary skill in the art would appreciate that the images may be manipulated with techniques known in the art, e.g., smoothing, and the dynamic range (intensity range) may be adjusted so that majority (e.g., >90%) of the fluorescent spots are counted, with minimum interference from background noises.

Such quantitative data may be analyzed with any method known in the art, such as using a histogram form, as shown in FIG. 3B, to provide insights into LRB and the endocytosis process. The histogram clearly shows the dramatic increase in the number of FM spots in the presence of ADP in the cell. The data in the histogram represent the total number of FM spots summed over all OSs. The histogram in FIG. 3C shows the distribution of the vesicles with the cell. Almost twice as many endocytic vesicles appear in the medulla, as compared with the periphery.

Because LRB-induced endocytosis is a common phenomenon, methods of the invention, as illustrated above, should also work with other ligands and/or receptors. This is demonstrated in FIGS. 4A and 4B, which show results from 5-HT (5-hydroxytryptamine) binding to its receptor.

Figure 4A:
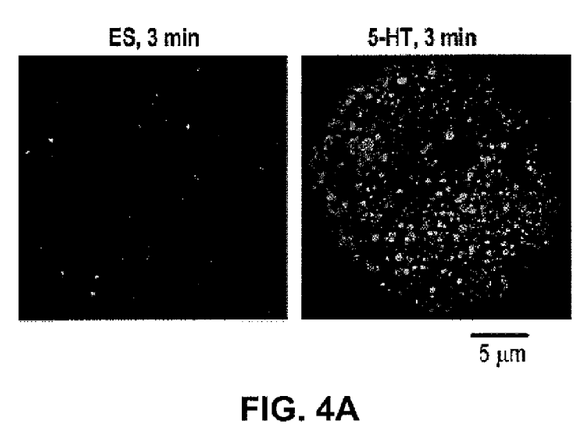
FIGS. 4A-4B show 5-HT-induced endocytosis in a DRG neuron visualized by the FEI technique and the data displayed in histogram.
Figure 4B:
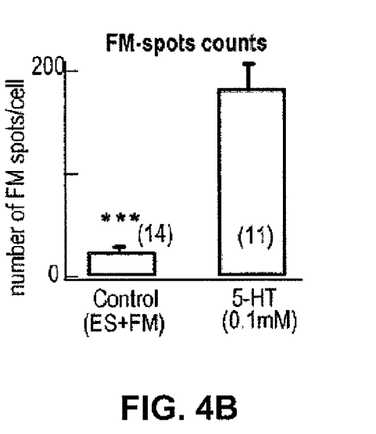

On the left panel of FIG. 4A is the FM image of the control cell (incubated with ES for 3 minutes) with very few visible FM spots. By contrast, 5-HT, (0.1 mM), shown in the right panel of FIG. 4A, induced substantial increases in endocytic vesicles distributed throughout the cytoplasm of the DRG neuron. FIG. 4B shows these results in a quantified form in a histogram.

Figure 5A:
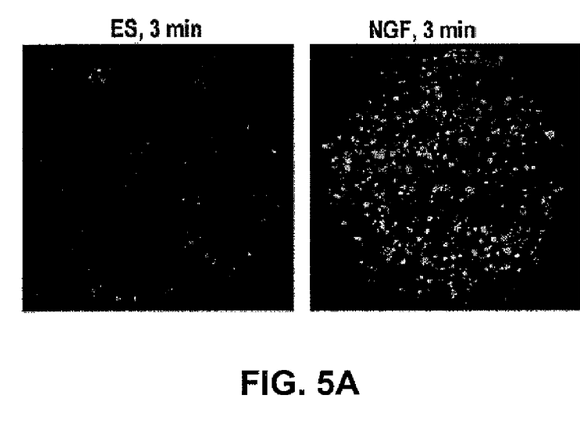
FIGS. 5A-5B show NGF-induced endocytosis in a DRG neuron visualized by the FEI technique and the data displayed in histogram.
Figure 5B:
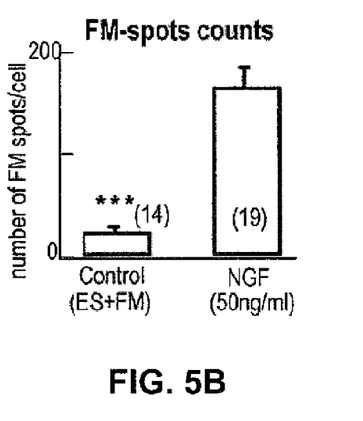

Methods of the invention, as described above, can also be applied to other membrane receptors not of the GPCR family, provided they also function by LRB-induced endocytosis. FIG. 5 shows an example of nerve growth factor (NGF) binding to a receptor of the tyrosine kinase (RTK) family. NGF is a pleiotropic neurotrophic protein implicated in the development, protection, and regeneration of NFG-sensitive neurons. It can bind to an RTK in the DRG neuron. As with ADP and 5-HT, FEI images demonstrate that NGF (50 ng/ml) induces a substantial increase in endocytic vesicles distributed throughout the cytoplasm. FIG. 5B shows these results in a quantified form in a histogram.

Figure 6A:
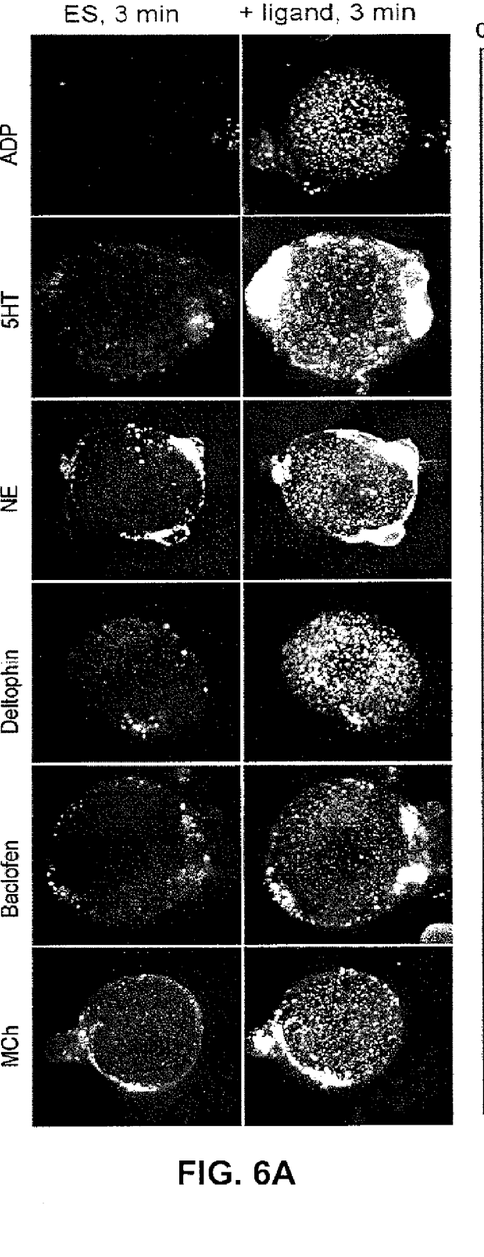
FIGS. 6A-6B show a method of the invention used to study different types and their relative abundance of various receptors in a DRG cell.
Figure 6B:
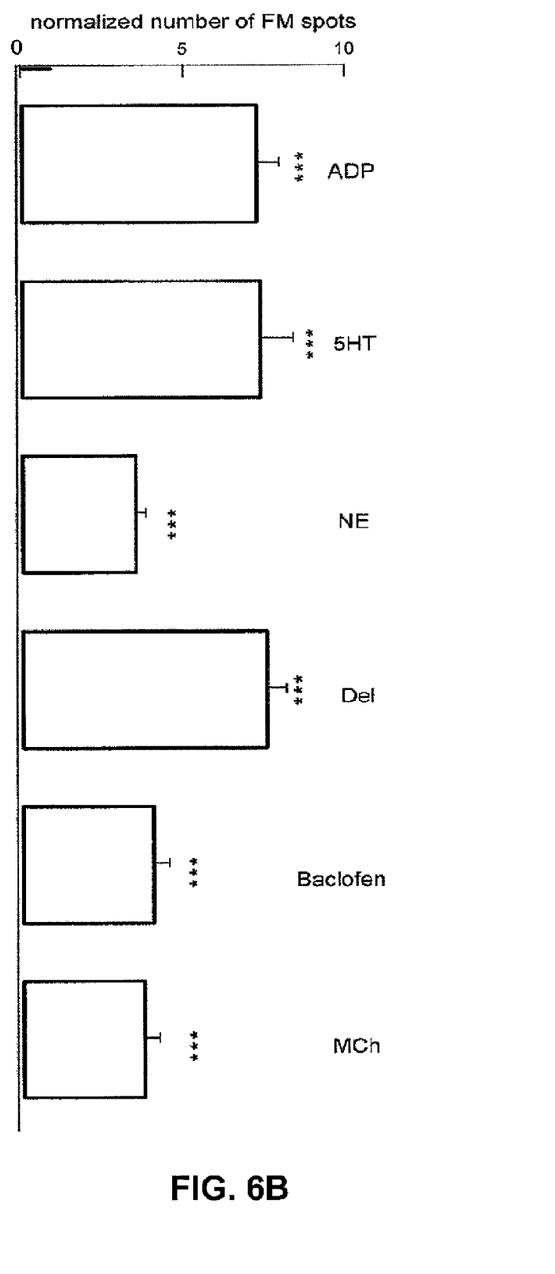

Using FEI, one may quantify the relative abundance of various GPCRs in a given cell. As shown in FIG. 6A, six different ligands for six different GPCR receptors on a DRG neuron were separately introduced and the number of FM spots counted (number FM spots corresponds to number of endocytic vesicles). In this experiment the GPCR-ligand pairs are: P2Y (ADP ligand), 5HT-R (5-HT ligand), muscarine Ach-mAChR (MCh ligand), $GABA_B$ (baclofen ligand), adrenaline-AR (NE ligand), and δ-opioid-DOR (deltorphin ligand). As shown in FIG. 6B, the number of FM spots induced by P2Y, 5HT-R, and DOR were 2-3 times higher than those induced by AR, $GABA_B$, and mAChR, indicating a greater abundance of the former on the DRG neuron.

As shown above, native cells may have multiple receptors that function via receptor internalization. These cells may not be ideal for screening drugs that act on a specific receptor. For such drug screening, it would be desirable to have cells that express only the target receptor. Cells that express a unique receptor may be naturally occurring or genetically engineered. Methods of the invention may also use cells the have been engineered to express a specific receptor. Methods for expressing a target receptor in a cell are well known in the art.

For example, heterologous expression of recombinant mammalian GPCRs in mammalian cells that do not normally express those receptors can provide a convenient means for studying receptor function or for identifying agonists and antagonists of those receptors. See e.g., U.S. Pat. No. 5,401,629, issued to Harpold et al., which discloses expression of human muscarinic receptor (HM1) in mouse cells. These types of ectopic expression studies have enabled researchers to study receptor signaling mechanisms and to perform mutagenesis studies which have been useful in identifying portions of receptors that are critical for ligand binding or signal transduction. In addition to such mechanism studies, such transfected cells are also useful for screening ligands (e.g., agonists) that bind to the specific receptor, in accordance with embodiments of the invention.

Time-Resolved FEI Recording

Methods of the invention, as noted above, can provide images of endocytic vesicles with relative ease. Thus, these methods for detecting LRB-induced endocytosis can be used in real time to monitor the endocytosis processes. Such a technique may be termed fluorescence intensity of FEI recording (FIF recording), as demonstrated in FIGS. 7A-7D. In real-time applications, the FEI methods described above may be modified as follows to provide better FIF results: (i) the spatial resolution can be reduced, i.e., OS thickness increased, to increase detection sensitivity; (ii) the confocal scan can be made at a fixed z-position (normally near the middle of the cell); and (iii) cell images can be obtained in the presence of extracellular FM dye (i.e., no need to wash away the dye outside the cells). Under these conditions, FIF recording can rapidly acquire many x-y images of the cell after ligand binding in order to monitor the LRB induced events in real time.

Figure 7:
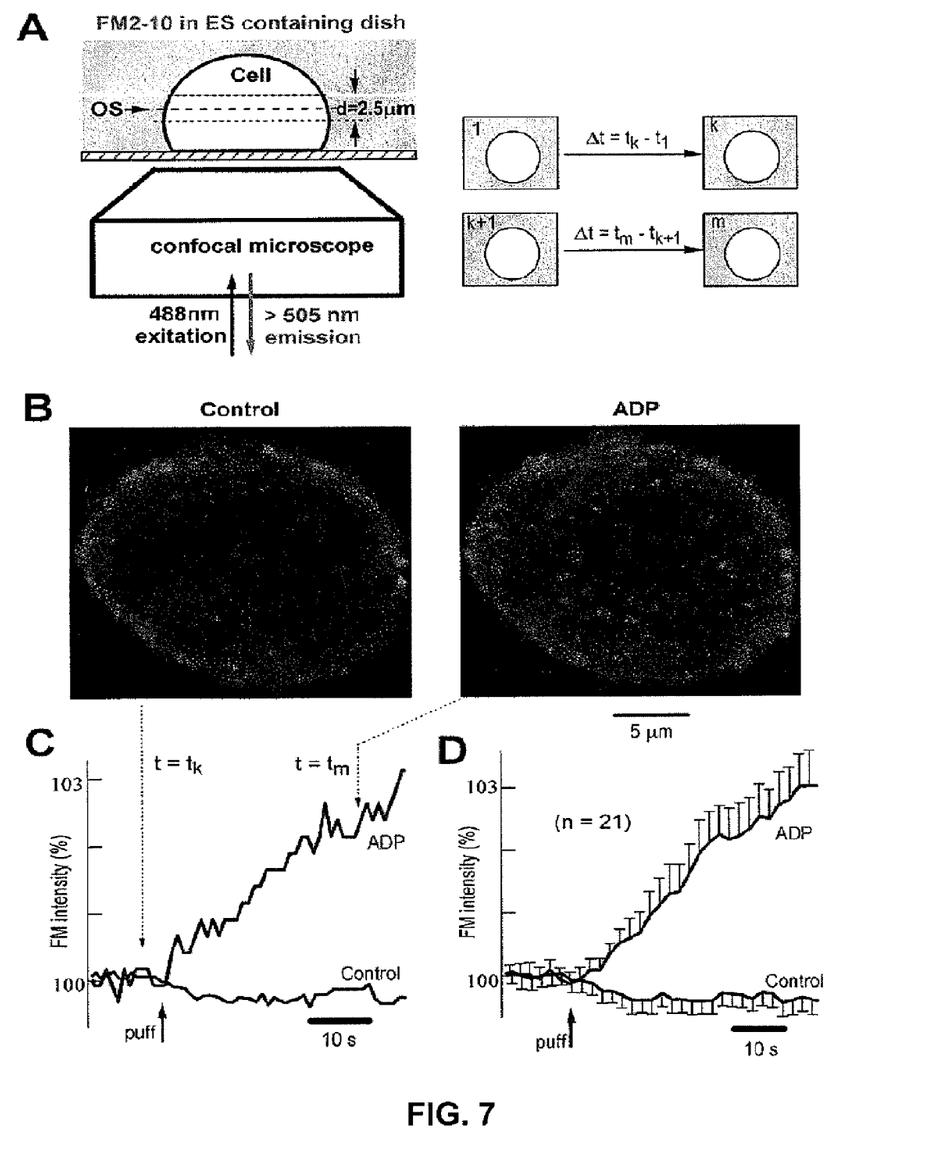
FIGS. 7A-7D illustrate a method of the invention used to monitor ligand binding and endocytosis in a time resolved fashion.

FIG. 7A illustrates a setup for performing a real-time recording of LRB-induced events. As illustrated, the cell is bathed in an ES solution containing a fluorescent dye (e.g., FM2-10), and the OS is selected to a thickness of about 2.5 mm to have a better sensitivity. The time course schematic on the right panel shows that from image frame 1 through image frame k (i.e., from $t_1$ through $t_k$), the cell is incubated with the ES solution only. This is to provide background readings before the ligand is added. From image frame K+1 to image frame m (i.e., from $t_{k+1}$ to $t_m$), the cell is incubated with the ligand (ADP) in the ES solution. These images provide insights into what happens after the ligand binds to the cell.

FIG. 7B show the images corresponding to $t=t_k$ (control) and $t=t_m$ (ADP) of a DRG neuron. The control image is taken right before the addition of the ligand, ADP, while the "ADP" image is taken towards the end of the ligand incubation period. It is evident that the ligand binding induced a substantial increase in the number of fluorescent spots (endocytic vesicles) in the cell.

FIG. 7C shows a typical time course, illustrating the intensities of FM images as a function of time. The fluorescence intensity is proportional to the total number of endocytic vesicles. FIG. 7D shows a time course for an average of 21 experiments. These results clearly show that addition of ADP significantly increases the fluorescence intensity (i.e., the number of endocytic vesicles) inside the cell. It is also apparent that the LRB-induced endocytosis occurs over a time course of several seconds. Therefore, the sampling rate of FIF recording can be 1 Hz or slower. These results show that a method of the invention as described above may be used to monitor the LRB-induced endocytosis in real time.

Differential FEI Labeling

The above examples of imaging the endocytic vesicles show that the spatial resolution of the images is sufficient to allow one to investigate different compartments in the cell. This capability, for example, may be used to probe the vesicle sorting or trafficking inside the cells. It is known that GPCRs are active cargos for the internalized vesicles, and each different type of GPCR vesicles may have its own sorting pathway. To investigate different sorting paths of vesicles internalized under different conditions (time, ligand, etc.), vesicles can be labeled with FM dyes of different colors in the same cell.

Figure 8:
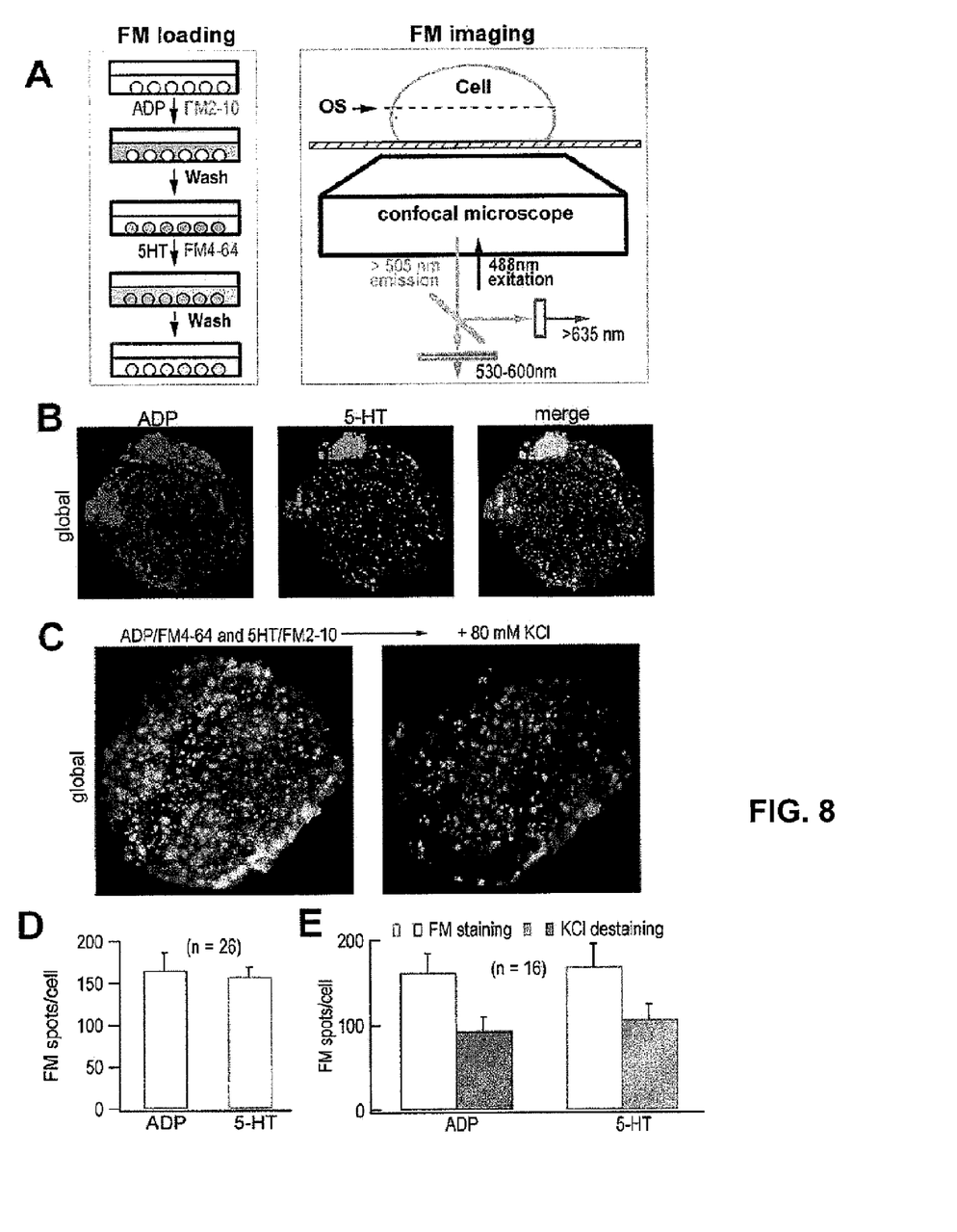
FIGS. 8A-8E illustrate a method of the invention used to monitor different ligand bindings to the receptors on the same cell using different fluorescent dyes.

FIG. 8A shows a schematic of labeling the cell with two different kinds of dyes. As shown in the left panel, the cells in a dish is incubated with ADP and FM2-10 (green fluorophore). Then, the dye and ADP are washed away and a second incubation is performed with 5-HT and FM4-64 (red fluorophone). The cells are again washed and monitored with a confocal microscope, as illustrated in the right panel. Both FM2-10 and FM4-64 can be excited with a light at 488 nm. The emission of FM2-10 can be monitored at 530-600 nm, while the emission of FM4-64 can be monitored at >635 nm.

With reference to FIG. 8B, ADP- and 5-HT-induced endocytic vesicles can be separately imaged with red FM4-64 and green FM2-10, respectively. The numbers of endocytic vesicles induced by these two ligands seem to be similar (FIG. 8D), confirming that the numbers of the receptors for ADP and 5-HT are about the same in DRG (see FIG. 6B). The merged FM image shows that most green and red FM spots are distributed as separate vesicles throughout the cytoplasm, indicating different sorting pathways for the ADP-induced vesicles and the 5-HT-induced vesicles.

To test whether there is a common sorting pathways for the ADP-induced and 5-HT-induced endocytic vesicles, the cell was treated with 80 mM KCL for three minutes. FIG. 8C shows a significant amount of vesicles were lost after the KCl treatment. FIG. 8E shows that about 43% of the red/P2Y vesicles and about 37% of the green/5HT-R vesicles were discharged. This observation suggests that about 40% of the endocytic vesicles induced by ADP and 5-HT have a common sorting pathway, which sends them into the readily releasable vesicle pool (RRP), which can be discharged by later action potentials.

High-Throughput Methods for Drug Discovery

The above description clearly shows that methods of the invention can provide sensitive, time and spatial resolved imaging for LRB-induced endocytosis. Because membrane receptors are often targets for therapeutics, methods of the invention can be useful in screening drugs that can bind to specific receptors.

High-throughput screening (HTS) has become a pivotal part of drug discovery for identifying potential lead molecules for specific disease targets. The success of screening is measured by several factors, including the throughput and costs of the assays, but ultimately by how many of the HTS hits progress forward through the drug discovery pipeline. Miniaturization of assays by conversion from 96- to 384- to 1536-wells to well-less platforms, and the utilization of automated equipment are methodologies implemented to increase the throughput and reduce the cost of the screen.

With a rapid method for the detection of endocytic vesicles in a single cell, it becomes possible to use the FEI technique as a rapid drug/ligand bioassay. Since FEI is an optical assay, it should be well-suited to automated high-throughput drug discovery to find therapeutics for the treatment of diseases associated with receptors that are subject to LRB-induced endocytosis.

Example of Multi-Well Protocol

Figure 9:
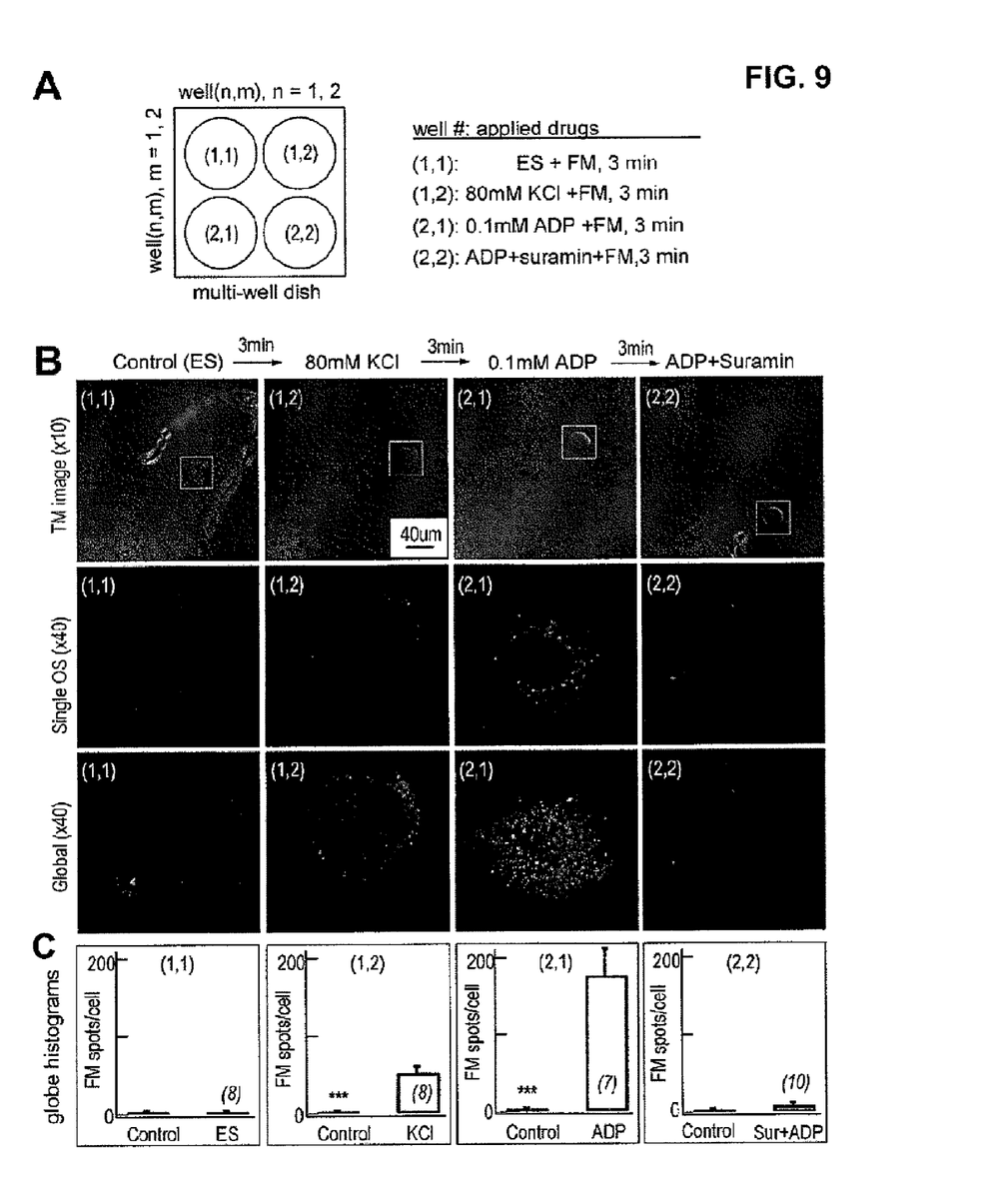
FIGS. 9A-9C illustrate a method of the invention used in a multi-well plate format to screen for ligand binding and endocytosis.

FIGS. 9A-9B illustrate a method of the invention that could be used for high throughput evaluation of LRB-induced endocytosis in a multi-well (here 2×2) format. The multi-well plate is the same as a standard cell culture plate, except that a 0.17 mm-thick glass cover-slip constitutes part of the bottom in each well. In this example, single DRG cells were plated on the cover-slips in the wells.

As illustrated in FIG. 9A, the four wells are incubated with four different kinds of reagents. Well (1,1) is incubated with ES and FM, without any ligand. Well (1,2) is incubated with 80 mM KCl and FM. Well (2,1) is incubated with 0.1 mM ADP and FM. Well (2,2) is incubated with ADP, Suramin, and FM. The incubations are all performed for 3 minutes.

Each well was scanned in sequence to obtain the images shown in FIG. 9B, and the endocytic signal (FM spots/cell) were analyzed and presented in histograms (FIG. 9C). In FIG. 9B, four columns of images correspond to four different wells, hence four different treatments. Within each column, the top image is a transmission microscopy image, showing the cells in the well. The cell bracketed by the square in each well is chosen for image analysis.

The selected cells are scanned for FM images of single OSs (middle image) as well as the global image (bottom image) in each cell (FIG. 9B). FIG. 9C shows the results in histograms that show the extents of LRB (i.e., endocytosis) in the wells. It is clear that ADP induced significant endocytosis, which can be inhibited by suramin, which is a highly specific protein tyrosine phosphatase inhibitor.

Although this protocol was performed manually with a 4 well plate, it is understood by those skilled in the art that a similar protocol could be applied to any multi-well plates, such as 96 wells or more. Furthermore, one could combine an electronic positioning system to synchronize well positioning, cell plating, ligand delivery/washing, FM imaging, and/or FM analysis so that some or all of the steps in the ligand/drug screening process can be automated. With cells from a cell line having the desired receptor (e.g., a GPCR or RTK) plated in a multi-well plate, individual testing agents can be tested in different wells. The ligand that produces abundant FM spots (i.e., endocytosis) in a particular well can be identified as a potential ligand for the receptor.

Some embodiments of the invention provide systems to perform the above described methods automatically. These systems take advantages of recent advances in instrumentation. See e.g., Taylor et al., American Scientist, 80: 322-335 (1992), which describes many of these methods and their applications. For example, Proffitt et. al. (Cytometry 24: 204-213 (1996)) describe a semi-automated fluorescence digital imaging system for quantifying relative cell numbers in situ in a variety of tissue culture plate formats, including 96-well microtiter plates. Furthermore, U.S. Pat. No. 6,875,578 issued to Giuliano et al. discloses a fluorescence-based system that can be used to analyze individual cells.

In accordance with embodiments of the invention, a system may consist of a confocal microscope (or any other suitable microscope) with a motorized stage, a video camera, and a microcomputer with a suitable software. The computer and the software are used to control the motorized stage, to scan the plate, and to take images. In addition, the software may be used to analyze image and calculate total fluorescence. The system, including the motorized stage, may be configured for a variety of tissue culture plate formats, such as the commonly used the 96-well format.

In addition, a system of the invention may include an automated fluid control/delivery (pipetting) system. Many commercially available fluid control systems are suitable for such purposes, including the MPS-2 described above.

Figure 10:
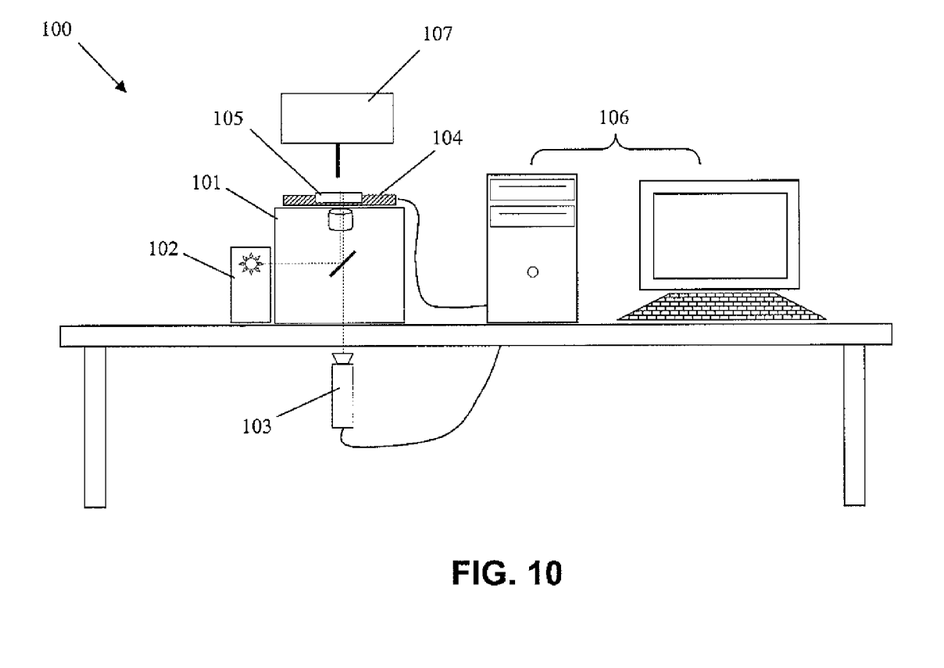
FIG. 10 illustrates a schematic of an automatic system for high throughput screening using a method of the invention.

FIG. 10 shows a schematic of a cell screening system 100 in accordance with one preferred embodiment of the invention. As shown, the screening system 100 comprises a fluorescence imaging system 101 having a microscope, an XY stage 104 adapted for holding a plate 105 and having a means for moving the plate to align the locations with the microscope and a means for moving the plate in the direction to effect focusing; an imaging device 103 (e.g., a digital camera); a light source 102 having optical means for directing excitation light to cells in the array of locations and a means for directing fluorescent light emitted from the cells to the imaging device (camera); and a computer system 106 for receiving and processing digital data from the camera. The computer system 106 is equipped for capturing images from the camera 103 and includes a display and an input device (e.g., keyboard and/or mouse) for user interaction. The computer system 106 may further include digital storage media for data storage and archiving, and means for control, acquisition, processing and display of results. It should be understood that some of these functions (e.g., data storage or analysis) may be provided by a separate computer. In addition, the cell screening system 100 may also include a microfluidic delivery/dispensing system 107 for the addition of reagents to the wells or removal of fluids from the wells.

In the example shown in FIG. 10, an inverted fluorescence microscope system 101 is used. Any suitable microscope may be used, including a Zeiss Axiovert inverted fluorescence microscope. The light source 102, for example, may be a 100 W mercury-arc lamp or 75 W xenon lamp. The XY stage 104 is configured to move the plate 105 in the XY directions over the microscope objective. The imaging device 103 is preferably a high resolution digital camera.

It should be noted that high throughput "whole plate" reader systems are known in the art and are commonly used as a component of high-throughput screening systems for screening large numbers of compounds. See e.g., Beggs, J. of Biomolec. Screening 2:71-78 (1997), and Macaffrey et al., J. Biomolec. Screening 1:187-190 (1996). However, cell screening systems in accordance with embodiments of the invention are for imaging individual cells in individual wells. A system of the invention can provide spatial resolution that is not possible with the "whole plate" readers.

A system of the invention, by providing convenient methods for high throughput screening of ligand-receptor bindings, can significantly improve drug candidate screening. As noted above, methods of the invention can provide high spatial and temporal resolution to monitor receptor internalization after ligand binding. This capability makes it possible to measure the effects of drugs on complex molecular events such as signal transduction pathways, as well as cell functions including, for example, apoptosis, cell division, cell adhesion, locomotion, exocytosis, and cell-cell communication. In addition, by using multicolor fluorescence, it becomes possible to assay multiple targets and cell processes in a single screening. Cross-correlation of cellular responses may yield a wealth of information required for target validation and lead optimization.

Advantages of embodiments of the invention include one or more of the following. Methods of the present invention can provide a rapid optical bioassay to screen for ligand bindings to membrane bound receptors. These methods are generally applicable to any receptor that can undergo endocytosis upon ligand binding. These methods can be used in HTS to screen for therapeutic agents that target various types of receptors that are internalized upon ligand binding. Many of such receptors have been shown to be involved in disease processes. Embodiments of the invention also offer an automated screen system that can be used in HTS for potential pharmaceuticals.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for detecting ligand binding to a membrane receptor, comprising the steps of:
    incubating a cell with a mixture of a dye and a ligand; and
    detecting dye-containing endocytic vesicles in the cell, wherein detection of the dye-containing endocytic vesicles at a level higher than a background level indicates said ligand binding to said membrane receptor, wherein the background level is obtained by incubating the cell with the dye in the absence of the ligand.

2. The method of claim 1, further comprising washing the cell, after the incubating step and before the detecting step, to remove the dye outside the cell.

3. The method of claim 1, wherein the dye is a fluorescence dye.

4. The method of claim 1, wherein the membrane receptor is a G-protein coupled receptor or a receptor of the tyrosine kinase family.

5. The method of claim 1, wherein the detecting step is performed with a microscope.

6. The method of claim 5, wherein the microscope is a confocal microscope.

7. The method of claim 6, wherein the detecting step is performed at one or more optical slices.

8. The method of claim 3, further comprising the step of obtaining one or more images of the dye-containing endocytic vesicles in the cell.

9. The method of claim 3, further comprising the step of quantifying the dye-containing endocytic vesicles in the cell.

10. The method of claim 1, wherein the detecting step is performed as a function of time.

11. The method of claim 1, wherein the method is performed in individual wells of a multi-well plate.

12. The method of claim 11, wherein the steps are performed with an automated apparatus.

13. The method of claim 2, further comprising the steps of:
    incubating the cell with a second dye and a second ligand, after the washing step; and
    washing the cell to remove the second dye and the second ligand remaining outside the cell, before the detecting step.

* * * * *

UNITED STATES PATENT AND TRADEMARK OFFICE
CERTIFICATE OF CORRECTION

PATENT NO. : 7,803,563 B2  
APPLICATION NO. : 12/298988  
DATED : September 28, 2010  
INVENTOR(S) : Zhuan Zhou et al.

Page 1 of 1

It is certified that error appears in the above-identified patent and that said Letters Patent is hereby corrected as shown below:

On the cover page, Item (75) Inventors, the second Inventors name appears as "Hoping Cheng" and should read as --H<u>e</u>ping Cheng--.

Signed and Sealed this  
Twenty-fifth Day of January, 2011

David J. Kappos  
*Director of the United States Patent and Trademark Office*